US00PP24860P2

(12) United States Plant Patent
Kobayashi

(10) Patent No.: US PP24,860 P2
(45) Date of Patent: Sep. 9, 2014

(54) POINSETTIA PLANT NAMED 'PER2010'

(50) Latin Name: ***Euphorbia pulcherrima* Willd.**
Varietal Denomination: PER2010

(71) Applicant: Ruth Kobayashi, Carlsbad, CA (US)

(72) Inventor: Ruth Kobayashi, Carlsbad, CA (US)

(73) Assignee: Ecke Ranch B.V., DeLier (NL)

( * ) Notice: Subject to any disclaimer, the term of this patent is extended or adjusted under 35 U.S.C. 154(b) by 3 days.

(21) Appl. No.: 13/694,962

(22) Filed: Jan. 22, 2013

(51) Int. Cl.
*A01H 5/00* (2006.01)

(52) U.S. Cl.
USPC ..... Plt./303

(58) Field of Classification Search
USPC ..... Plt./303
See application file for complete search history.

*Primary Examiner* — Anne Grunberg
(74) *Attorney, Agent, or Firm* — C. A. Whealy

(57) ABSTRACT

A new and distinct cultivar of Poinsettia plant named 'PER2010', characterized by its relatively compact, upright and mounded plant habit; moderately vigorous growth habit; freely and upright branching habit; dark green-colored leaves; early-season flowering response; large inflorescences with dark red-colored flower bracts with random light red-colored flecks; and good post-production longevity.

1 Drawing Sheet

Botanical designation: *Euphorbia pulcherrima* Willd.
Cultivar denomination: 'PER2010'.

CROSS REFERENCED TO CLOSELY-RELATED APPLICATIONS

Title: Poinsettia Plant Named 'PER2110'
Applicant: Ruth Kobayashi
Filed: Concurrently with this application having U.S. Plant patent application Ser. No. 13/694,963

BACKGROUND OF THE INVENTION

The present invention relates to a new and distinct cultivar of Poinsettia plant, botanically known as *Euphorbia pulcherrima* Willd., and hereinafter referred to by the name 'PER2010'.

The new Poinsettia plant is a product of a planned breeding program conducted by the Inventor in Encinitas, Calif. The objective of the breeding program is to create new uniform Poinsettia plants having large inflorescences with attractive flower bracts and excellent post-production longevity.

The new Poinsettia plant originated is a naturally-occurring whole plant mutation of *Euphorbia pulcherrima* Willd. 'PER1188', disclosed in U.S. Plant Pat. No. 23,201. The new Poinsettia plant was discovered and selected by the Inventor as a single flowering plant from within a population of plants of 'PER1188' in a controlled greenhouse environment in Encinitas, Calif. on Sep. 22, 2009.

Asexual reproduction of the new Poinsettia plant by terminal vegetative cuttings in a controlled greenhouse environment in Encinitas, Calif. since January, 2010 has shown that the unique features of this new Poinsettia plant are stable and reproduced true to type in successive generations of asexual reproduction.

SUMMARY OF THE INVENTION

Plants of the new Poinsettia have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER2010'. These characteristics in combination distinguish 'PER2010' as a new and distinct Poinsettia plant:

1. Relatively compact, upright and mounded plant habit.
2. Moderately vigorous growth habit.
3. Freely and upright branching habit.
4. Dark green-colored leaves.
5. Early-season flowering response; under natural season conditions, plants flower in early November in Southern California.
6. Large inflorescences with dark red-colored flower bracts with random light red-colored flecks.
7. Good post-production longevity.

In side-by-side comparisons conducted in Encinitas, Calif., plants of the new Poinsettia differ primarily from plants of the parent, 'PER1188', in flower bract color as plants of 'PER1188' have bright red-colored flower bracts with no flecking.

Plants of the new Poinsettia can be compared to plants of the *Euphorbia pulcherrima* Willd. 'PER2110', disclosed in U.S. Plant patent application Ser. No. 13/694,963. Plants of the new Poinsettia and 'PER2110' differ primarily in flower bract color.

Plants of the new Poinsettia can be compared to plants of the *Euphorbia pulcherrima* Willd. '490 Jingle Bells', disclosed in U.S. Plant Pat. No. 8,771. In side-by-side comparisons conducted in Encinitas, Calif., plants of the new Poinsettia differed primarily from plants of '490 Jingle Bells' in the following characteristics:

1. Plants of the new Poinsettia were more compact than plants of '490 Jingle Bells'.
2. Branching habit of plants of the new Poinsettia was more upright than branching habit of plants of '490 Jingle Bells'.
3. Plants of the new Poinsettia flowered about eleven days earlier than plants of '490 Jingle Bells' when grown under natural season conditions.
4. Plants of the new Poinsettia and '490 Jingle Bells' differed slightly in flower bract color.

Plants of the new Poinsettia can also be compared to plants of the *Euphorbia pulcherrima* Willd. 'PER5499', disclosed in U.S. Plant Pat. No. 15,917. In side-by-side comparisons conducted in Encinitas, Calif., plants of the new Poinsettia differed primarily from plants of 'PER5499' in the following characteristics:

1. Plants of the new Poinsettia were more compact than plants of 'PER5499'.
2. Plants of the new Poinsettia had darker green-colored leaves than plants of 'PER5499'.
3. Plants of the new Poinsettia flowered about 15 days earlier than plants of 'PER5499' when grown under natural season conditions.
4. Plants of the new Poinsettia and 'PER5499' differed in flower bract color as plants of 'PER5499' had red-colored flower bracts with white-colored random flecks.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet comprises a side perspective view of a typical flowering plant of 'PER2010' grown in a container.

The photograph at the top of the sheet is a close-up view of a typical flowering plant of 'PER2010'.

DETAILED BOTANICAL DESCRIPTION

Plants used in the aforementioned photographs and in the following detailed description were grown during the late autumn/early winter in 16.5-cm containers in a polyethylene-covered greenhouse in Encinitas, Calif. and under natural season conditions and cultural practices typical of commercial Poinsettia production. During the production of the plants, day temperatures averaged 24° C., night temperatures averaged 18° C. and light levels averaged 5,000 foot-candles. Measurements and numerical values represent averages for typical flowering plants. Plants were pinched one time and were 17 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER2010'.

Parentage: Naturally-occurring whole plant mutation of *Euphorbia pulcherrima* Willd. 'PER1188', disclosed in U.S. Plant Pat. No. 23,201.

Propagation:

*Type*.—Terminal vegetative cuttings.

*Time to initiate roots*.—About seven to ten days at 20° C. night temperature and 27° C. day temperature.

*Time to produce a rooted young plant*.—About four weeks at 20° C. night temperature and 27° C. day temperature.

*Root description*.—Fibrous; white in color.

Plant description:

*Plant habit and form*.—Relatively compact, upright and mounded plant habit; inverted triangle; large inflorescences positioned above the foliar plane; moderately vigorous growth habit.

*Plant height*.—About 34 cm.

*Plant diameter or spread*.—About 58 cm.

*Lateral branch description*.—Quantity: Freely branching habit, about eight lateral branches develop after pinching. Length: About 28 cm. Diameter: About 7 mm. Internode length: About 2.2 cm. Strength: Strong. Texture: Smooth, glabrous. Color: Close to 146B.

*Leaf description*.—Arrangement: Alternate, simple. Length: About 11.6 cm. Width: About 9 cm. Shape: Broadly lanceolate, lobed. Apex: Acuminate. Base: Rounded. Margin: Mostly entire with pointed lobes. Aspect: Flat. Venation pattern: Pinnate, arcuate. Texture, upper surface: Smooth, glabrous. Texture, lower surface: Pubescent. Color: Developing leaves, upper surface: Close to N137A. Developing leaves, lower surface: Close to 137B. Fully expanded leaves, upper surface: Close to 139A; venation, close to 137A. Fully expanded leaves, lower surface: Close to N137C; venation, close to 147C. Petiole: Length: About 5.5 cm. Diameter: About 3 mm. Texture, upper and lower surfaces: Smooth, glabrous. Color, upper surface: Close to 183A. Color, lower surface: Close to 176B.

Inflorescence description:

*Inflorescence type and habit*.—Terminal inflorescences are compound corymbs of cyathia with colored flower bracts subtending the cyathia; inflorescences uniformly positioned above the foliar plane.

*Fragrance*.—None detected.

*Flowering response*.—Early-season flowering response; under natural season conditions, plants typically flower on November 7 in Southern California; under artificial long nyctoperiod/short photoperiod conditions, plants flower about 7 to 7.5 weeks later.

*Post-production longevity*.—Good post-production longevity; plants of the new Poinsettia maintain good substance and flower bract color for about four weeks under interior conditions; inflorescences persistent.

*Inflorescence diameter*.—About 30 cm.

*Inflorescence height* (*depth*).—About 8.5 cm.

*Flower bracts*.—Quantity per inflorescence: About 20. Length, largest bracts: About 14.4 cm. Width, largest bracts: About 9.8 cm. Shape: Broadly lanceolate, occasionally lobed. Apex: Acuminate. Base: Rounded. Margin: Entire, occasionally with three to four shallow lobes. Texture, upper surface: Slightly rugose, glabrous. Texture, lower surface: Veins prominent, glabrous. Aspect: Mostly horizontal. Venation pattern: Pinnate, arcuate. Color: Developing or transitional bracts, upper surface: Close to 46A;

venation, close to 146A to 146C. Developing or transitional bracts, lower surface: Close to 147B to 147C tinted with close to N34C. Fully expanded bracts, upper surface: Close to 46B with random flecks, close to 53C to 53D; venation, close to 46B; color does not change with development. Fully expanded bracts, lower surface: Close to 47A with random flecks, close to 53D; venation, close to 47A. Bract petiole: Length: About 3.7 cm. Diameter: About 2.5 mm. Texture, upper and lower surfaces: Smooth, glabrous. Color, upper and lower surfaces: Close to 47A.

*Cyathia*.—Quantity per corymb: About 14. Length: About 1.1 cm. Width: About 6 mm. Shape: Ovoid. Texture: Smooth, glabrous. Color, immature: Close to 146A. Color, mature: Close to 146B to 146C.

*Nectaries*.—Quantity per cyathium: One. Length: About 4 mm. Width: About 2.5 mm. Shape: Elliptical. Texture: Smooth, glabrous. Color: Close to 21D.

*Peduncles*.—Length: About 4 mm. Diameter: About 2 mm. Strength: Strong. Aspect: Mostly upright. Texture: Smooth, glabrous. Color: Close to 145A.

*Reproductive organs*.—Stamens: Quantity per cyathium: About eight to ten. Filament length: About 5 mm. Filament color: Close to 58A. Anther shape: Oval; bi-lobed. Anther length: About 1 mm. Anther color: Close to 59B. Amount of pollen: Scarce. Pollen color: Close to 15C. Pistils: Pistil development has not been observed on plants of the new Poinsettia.

*Seeds and fruits*.—Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER2010' as illustrated and described.

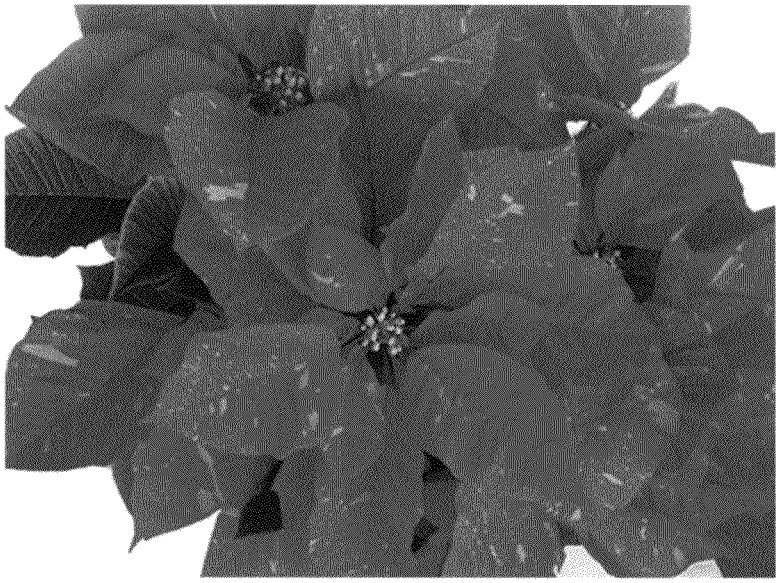
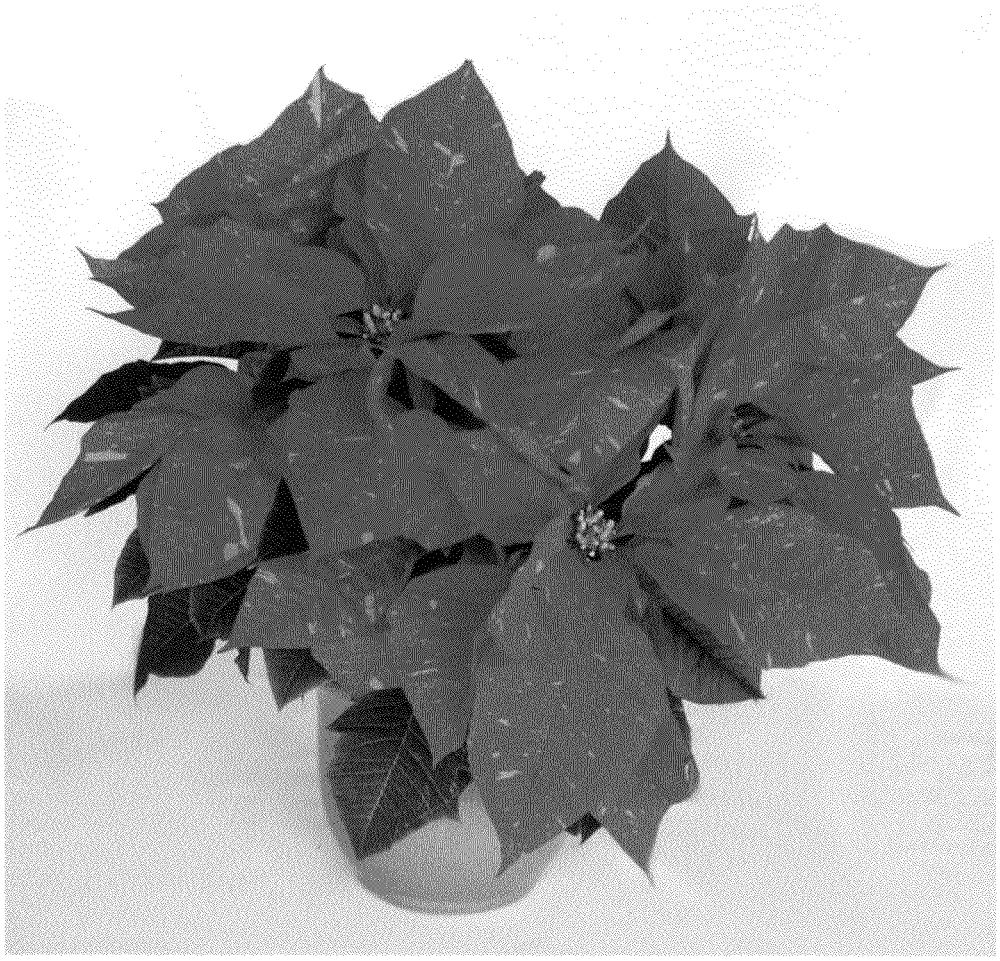

* * * * *